(12) United States Patent
Li et al.

(10) Patent No.: US 6,503,206 B1
(45) Date of Patent: Jan. 7, 2003

(54) APPARATUS HAVING REDUNDANT SENSORS FOR CONTINUOUS MONITORING OF VITAL SIGNS AND RELATED METHODS

(75) Inventors: Luya Li, Coquitlam (CA); Yunquan Chen, Delta (CA); Rakesh Kumar Sethi, Vancouver (CA); Ming Sun, New Westminster (CA)

(73) Assignee: VSM Medtech LTD, Vancouver (CA)

( * ) Notice: Subject to any disclaimer, the term of this patent is extended or adjusted under 35 U.S.C. 154(b) by 0 days.

(21) Appl. No.: 09/917,608

(22) Filed: Jul. 27, 2001

(51) Int. Cl.[7] .................................. A61B 5/02
(52) U.S. Cl. ................ 600/481; 600/483; 600/485; 600/300; 600/301
(58) Field of Search ................ 600/481, 483, 600/485, 372, 300, 301, 504, 500

(56) References Cited

U.S. PATENT DOCUMENTS

| | | | |
|---|---|---|---|
| 4,186,748 A | * 2/1980 | Schlager | 374/113 |
| 4,942,877 A | 7/1990 | Sakai et al. | |
| 5,544,651 A | * 8/1996 | Wilk | 600/310 |
| 5,645,059 A | 7/1997 | Fein et al. | |
| 5,938,593 A | * 8/1999 | Ouellette | 324/692 |
| 6,006,125 A | * 12/1999 | Kelly et al. | 600/382 |
| 6,241,679 B1 | 6/2001 | Curran | |
| 6,409,675 B1 | * 6/2002 | Turcott | 600/504 |

* cited by examiner

*Primary Examiner*—Max Hindenburg
*Assistant Examiner*—Navin Natnithithadha
(74) *Attorney, Agent, or Firm*—Oyen Wiggs Green & Mutala

(57) ABSTRACT

Apparatus for monitoring one or more vital signs of a subject has a number of sensors. There is at least one redundant sensor. Each sensor originates a signal. A selection system determines performance criteria for a number of groups of signals. Each group includes one or more signals. The apparatus computes a predicted value for a vital sign by either computing a value from each group of signals and taking a weighted average with weights based upon the performance criterion or by selecting one of the groups of signals for which the performance criterion is best and computing the output value from that group of signals. The output values are relatively insensitive to artifacts and to errors caused by the disconnection or malfunctioning of one sensor.

20 Claims, 3 Drawing Sheets

APPARATUS HAVING REDUNDANT SENSORS FOR CONTINUOUS MONITORING OF VITAL SIGNS AND RELATED METHODS

TECHNICAL FIELD

This invention relates to devices for monitoring vital signs such as blood pressure, pulse rate, and oxygen saturation. The invention has particular application in devices for determining blood pressure by measuring a pulse wave velocity or pulse transit time.

BACKGROUND

Equipment for monitoring the vital signs of subjects is widely used in clinical settings. Such devices may monitor various physiological signs including blood pressure, oxygen saturation, pulse rate and the like. Such devices typically include one or more sensors placed at suitable locations on the subject's body. Various different types of sensors may be used. The sensors may be of invasive types or of non-invasive types. Signals from the sensors are carried to the vital signs monitoring equipment where they are amplified, conditioned, and processed to determine values for the physiological parameters being measured.

In general, it is desirable to provide non-invasive monitoring of vital signs. While invasive systems are sometimes used, surgery is required to introduce sensors of invasive types into the subject's body. The sensors typically have leads which emerge from the subject's body through a fistula. The fistula can provide a pathway for infection.

As an example of non-invasive monitoring of a vital sign, blood oxygen saturation may be measured by providing a small clip-on sensor which includes one or more light sources and one or more light detectors. Variations in the oxygen saturation of the subject's blood cause resulting variations in the intensity of light reaching the detector. These variations are superimposed upon a variation in the intensity of light reaching the detector which results from the subject's heartbeat pulses. A device equipped with this type of sensor can also be used to measure pulse rate. Various such devices are known.

One type of system for measuring a subject's blood pressure relies upon the fact that the speed at which pulse waves propagate through a blood vessel is dependent upon blood pressure. Consequently, if one detects the arrival of a pulse at two different points of a subject's circulatory system there will be, in general, a difference in the time at which the pulse wave arrives at the two points. This time difference varies according to the blood pressure. One system for measuring blood pressure as a function of such a time difference is described in PCT application No. PCT/CA00/010552, and in the commonly owned and co-pending application entitled CONTINUOUS NON-INVASIVE BLOOD PRESSURE MONITORING METHOD AND APPARATUS which is being filed simultaneously herewith, both of which are fully incorporated herein by reference. Such systems require at least two sensors, one for detecting the arrival of the pulse wave at each of the two points. This type of device may use sensors of the same type as are used to detect oxygen saturation although other types of sensor could also be used.

One problem with such vital signs monitoring equipment is that the accuracy of measurements obtained can depend upon the stability of the signals received from the sensors. Artifacts may be caused by movement of the subject. In the worst case, a sensor may become disconnected from the subject and monitoring may be interrupted until the sensor is replaced.

There is a need for cost effective methods and apparatus for monitoring one or more vital signs of a subject which provide improved accuracy and are affected less by artifacts than current vital signs monitoring equipment.

SUMMARY OF INVENTION

This invention provides an apparatus for monitoring one or more vital signs of a subject by using a number of sensors. Each sensor originates a signal, typically a pulse signal. A selection system determines performance criteria for a number of groups of signals. Each group includes one or more signals. The apparatus computes a estimated value for a vital sign by either computing a value from each group of signals and taking a weighted average with weights based upon the performance criterion or by selecting one of the groups of signals for which the performance criterion is best and computing the output value from that group of signals.

The output values are relatively insensitive to artifacts and to errors caused by the disconnection or malfunctioning of one sensor. Further advantages and features of the invention are described below.

BRIEF DESCRIPTION OF DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
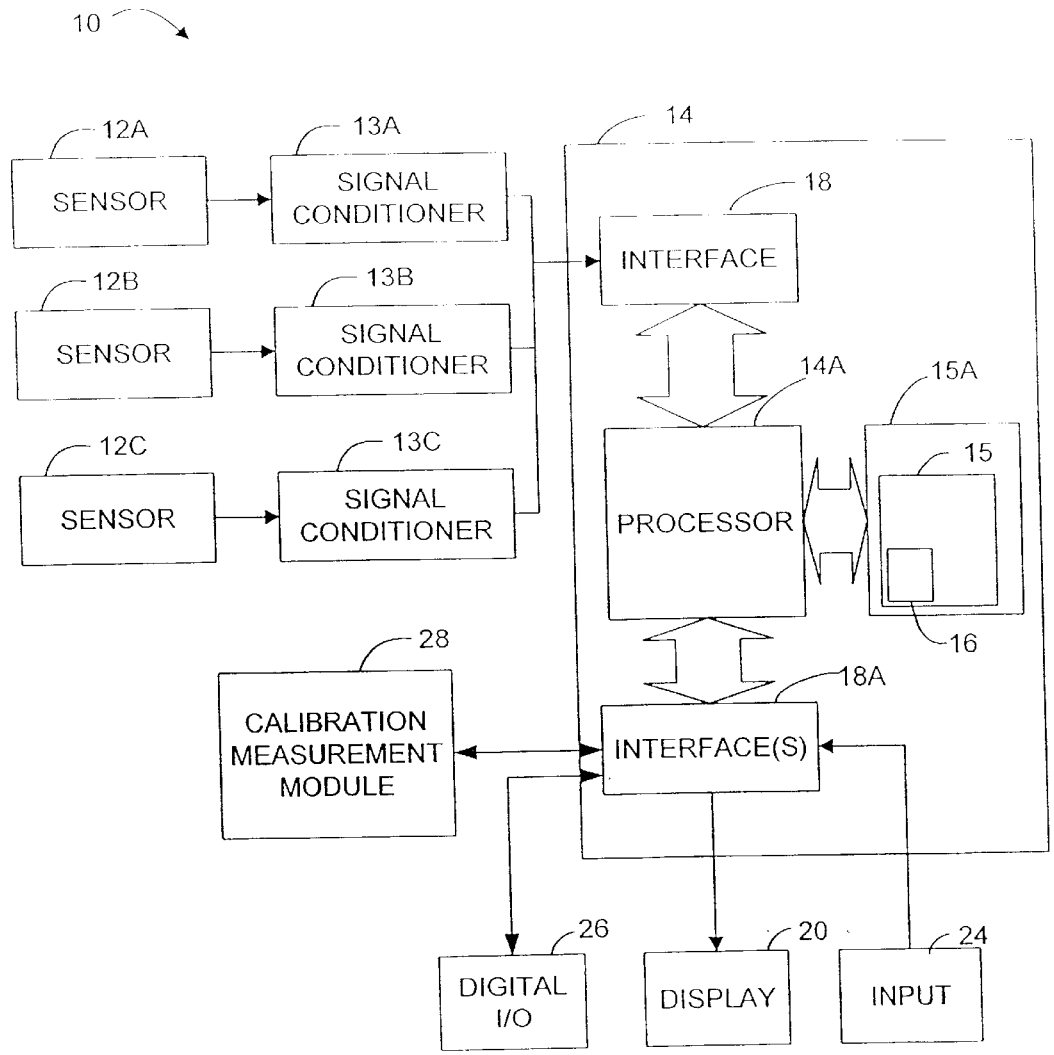
FIG. 1 is a block diagram of a vital signs monitoring system according to the invention.
Figure 2:
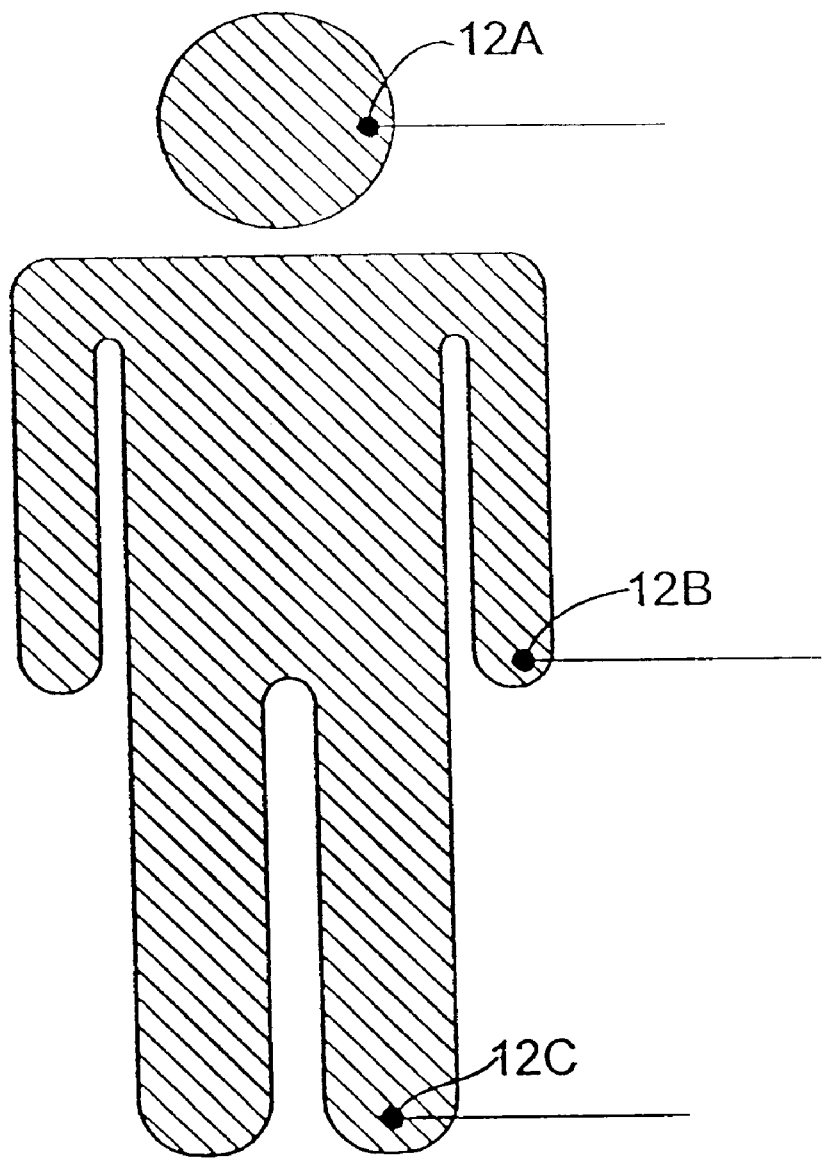
FIG. 2 is a view illustrating possible sensor locations for a vital signs monitoring system according to the invention; and, FIG. 3 is a block diagram of a vital signs monitoring system according to a specific embodiment of the invention.

FIG. 1 shows a system 10 according to the invention. FIG. 1 comprises a plurality of sensors 12. The illustrated embodiment comprises three sensors, 12A, 12B and 12C. As shown in FIG. 2, sensors 12A, 12B and 12C may be located on a subject's earlobe, finger and toe. Sensors 12 include at least one redundant sensor. That is, there is at least one more sensor 12 than is required for the type of measurement being made by system 10. The signal from each sensor 12 is conditioned and digitized in a signal conditioner 13. In the illustrated embodiment there are three separate signal conditioners 13A, 13B and 13C which correspond respectively with sensors 12A, 12B and 12C.

The resulting digitized signals are passed to a controller 14. In the illustrated embodiment of the invention, controller 14 comprises a processor 14A. Processor 14A runs software 15 stored in a program memory 15A. Software 15 receives the signals from all of sensors 12A through 12C by way of a suitable interface 18.

In the illustrated example there are three sensors. This means that there are three pairs of sensors. Software 15 computes a blood pressure for the subject from the signals of each of the three pairs of sensors. This yields three computed values for the subject's blood pressure. Computation of the subject's estimated blood pressure may be done, for example, according to the methods described in PCT patent application No. PCT/CA00/010552 which is incorporated herein by reference. The methods described in that application involve measuring a time difference between a pair of signals to obtain a differential pulse transit time (DPTT). Separate DPTT values are derived for systolic and diastolic portions of the signals. A known relationship between DPTT and blood pressure is used to compute an estimated blood pressure from a DPTT value. The known relationship is obtained during a calibration process which involves measuring the subject's blood pressure by a separate accurate mechanism, and substantially simultaneously measuring the DPTT. These methods may be separately applied to each pair of signals from sensors 12.

Controller 14 includes an automated selection system 16. Selection system 16 takes the signals from sensors 12 in distinct groups. In this case, "distinct" means that each group has a combination of signals from a different set of one or more sensors 12. Each group includes sufficient signals for the determination of a vital sign of interest. Where the groups include more than one signal, a signal from one sensor 12 may be included in more than one group. Selection system 16 identifies the best group of sensors 12 to be used for monitoring the vital sign in question. For example, where the vital sign is a blood pressure determined from a DPTT, each group of sensors comprises a pair of two sensors. For vital signs, such as pulse or blood oxygen saturation, which can be measured on the basis of the signal from one sensor the groups of sensors include one sensor each.

The determination of the best group of sensors to use is preferably made based upon the stability of the signals originating at the sensors. For example, the following equation may be used to provide a performance criterion for the pair of signals $(p_i, p_j)$ to be used in a DPTT blood pressure estimation:

$$C_{ij} = [\text{Corr}(p_i, p_j)/\sigma_i \sigma_j]_{max} \tag{1}$$

Where, $C_{ij}$ is the maximum value of the correlation coefficient of the paired signals $(p_i, p_j)$ and $\sigma_i$ and $\sigma_j$ are deviation measures for the two signals which are given as follows:

$$\sigma_i = \sqrt{\frac{1}{N-1} \sum_{k=0}^{N-1} [p_i(k) - \mu_i]^2} \tag{2}$$

$$\sigma_j = \sqrt{\frac{1}{N-1} \sum_{k=0}^{N-1} [p_j(k) - \mu_j]^2}. \tag{3}$$

The correlation function (Corr) between the two signals can thus be calculated as:

$$\text{Corr}(p_i, p_j) = \frac{1}{N} \sum_{k=0}^{N-1} [p_i(k) - \mu_i][p_j(k) - \mu_j] \tag{4}$$

where N is the number of samples used to calculate DPTT and determine the performance of the considered pair in a certain period of time. $\mu_i$ and $\mu_j$ are respectively average signal values for the paired signals from the sensors under consideration.

$\mu_i$ may be given by the following equation:

$$\mu_i = \frac{1}{N} \sum_{k=0}^{N-1} p_i(k) \tag{5}$$

$\mu_j$ may be given by the following equation:

$$\mu_j = \frac{1}{N} \sum_{k=0}^{N-1} p_j(k) \tag{6}$$

The performance criterion $C_{ij}$ given by equation (1) has a number of features which makes it suitable for use as a performance criterion for the pair of sensors under consideration. In particular, $C_{ij}$ is independent of the amplitudes of pulse signals $p_i$ and $P_j$ and $-1 \leq C_{ij} \leq 1$.

To reduce the complexity of these computations, a histogram-based calculation may be used in practice. Histogram-based calculation techniques which may be applied in this invention are described in Smith, "*The Scientist and Engineer's Guide to Digital Signal Processing (Second Edition)*" California Technical Publishing, 1999. Histogram-based techniques have the advantage that computational complexity is not dependent upon the number of samples collected.

Selection system 16 preferably comprises a function which tests for unacceptable signal values (as might result, for example, from the disconnection of a sensor) and, when such conditions are detected, forces the affected performance criterion $C_{ij}$ to be zero (or some other value that will cause the selection system 16 to not select the pairs of sensors affected by the unacceptable signal).

In the preferred embodiment of the invention, selection system 16 computes a blood pressure as a weighted average of the blood pressures computed from the signals of each of three pairs of sensors. This weighted average may be expressed as follows:

$$P = \sum_{ij} a_{ij} P_{ij} \tag{7}$$

Where there are three sensors, this reduces to:

$$P = a_{12}P_{12} + a_{23}P_{23} + a_{31}P_{31} \tag{8}$$

where $a_{12}$, $a_{23}$ and $a_{31}$ are weighting factors with $a_{12} + a_{23} + a_{31} = 1$ and $P_{12}$, $P_{23}$ and $P_{31}$ are blood pressures calculated from the signals produced by each of the three pairs of sensors respectively.

The weighting factors $a_{ij}$ (where i and j are indices which represent the sensors in the pair of sensors under consideration) may be given by the following equation, where $C_{ij}$ is the performance criterion for the pair of sensors under consideration:

$$a_{ij} = \frac{C_{ij}}{\sum_{ij} C_{ij}} \tag{9}$$

In the alternative, selection system 16 may select one of the pairs of sensors which provides the best value for the subject's blood pressure (i.e. for which the performance criterion is the highest). In this case, apparatus 10 presents the blood pressure derived from the signals of that pair of sensors 12 as the subject's blood pressure. This alternative embodiment of the invention is a special case of the weighted average according to equation (8) in which the values of $a_{ij}$ which do not correspond to the group of signals having the best performance criterion are all zero and the $a_{ij}$ corresponding to the group of signals having the best performance criterion is 1.

A display 20 displays the computed blood pressure. A user input device, 24 such as a button panel, a graphical user interface, a touch screen, or the like is provided to permit users to control the operation of apparatus 10. Preferably, user input device 24 permits a user to control whether selection system 16 selects signals from a specified pair of sensors 12, selects signals from the pair of sensors 12 which has the best performance criterion, or uses signals from all of sensors 12 in a blended average such as that of equation (7).

A digital input/output (I/O) connection 26 permits results to be delivered to other devices, for example, a printer, or a data collector/concentrator, or a computer being used for data analysis. A non-invasive blood pressure (NIBP) measurement module 28 provides reference blood pressures for calibration and re-calibration purposes. Display 20, user input 24, I/O connection 26 and measurement module 28 communicate with processor 14A by way of one or more suitable interfaces 18A.

Apparatus 10 according to the invention preferably uses a similar strategy to that described above for obtaining and displaying a value representing the oxygen saturation of a subject's blood and the subject's pulse rate. Each of the three sensors produces a signal which can be used to derive an oxygen saturation value and a pulse rate value. As the performance criteria are calculated in real time for CNIBP estimation, one signal can be selected from the best pair of sensors for the purpose of obtaining an oxygen saturation value and a pulse rate value.

Once again, the system may be set to display a best one of the oxygen saturation or pulse rate values or, in the alternative, may present an oxygen saturation value which is a blended average of the oxygen saturation or pulse rate values derived from the signals originating from each sensor.

Those skilled in the art will notice that system 10 has at least one redundant sensor. If any one sensor becomes disconnected or malfunctions then the signal performance of all parameter values which are calculated based upon a signal from that sensor will be poor or useless. Such values will be given either a very small weighting or no weighting at all in the computation of the parameter to be displayed. In the preferred embodiment of the invention, processor 14 causes apparatus 10 to generate a visual or audible warning if the performance criterion for one group of sensors is lower than a threshold value. Most preferably the visual or audible warning is generated if the performance criterion remains below the threshold value for longer than a predetermined time period.

It is preferable to re-calibrate system 10 relatively frequently. For example, it is preferable to compare the blood pressure values produced by system 10 to a calibration value obtained by another measurement technique approximately every 30 minutes. Re-calibration is especially important if a sensor is relocated. Re-calibration is also desirable if the extremities of the subject where sensors are located are moved in relation to the subject's heart. For example, if a sensor is on a subject's finger and the arm to which the finger is attached is elevated then it would be preferable to re-calibrate the system after the subject has assumed a comfortable position with the arm elevated. Similarly, if a vasoactive medication is administered to the subject, or the dose of a continuously delivered vasoactive medication is altered, re-calibration is desirable.

Figure 3:
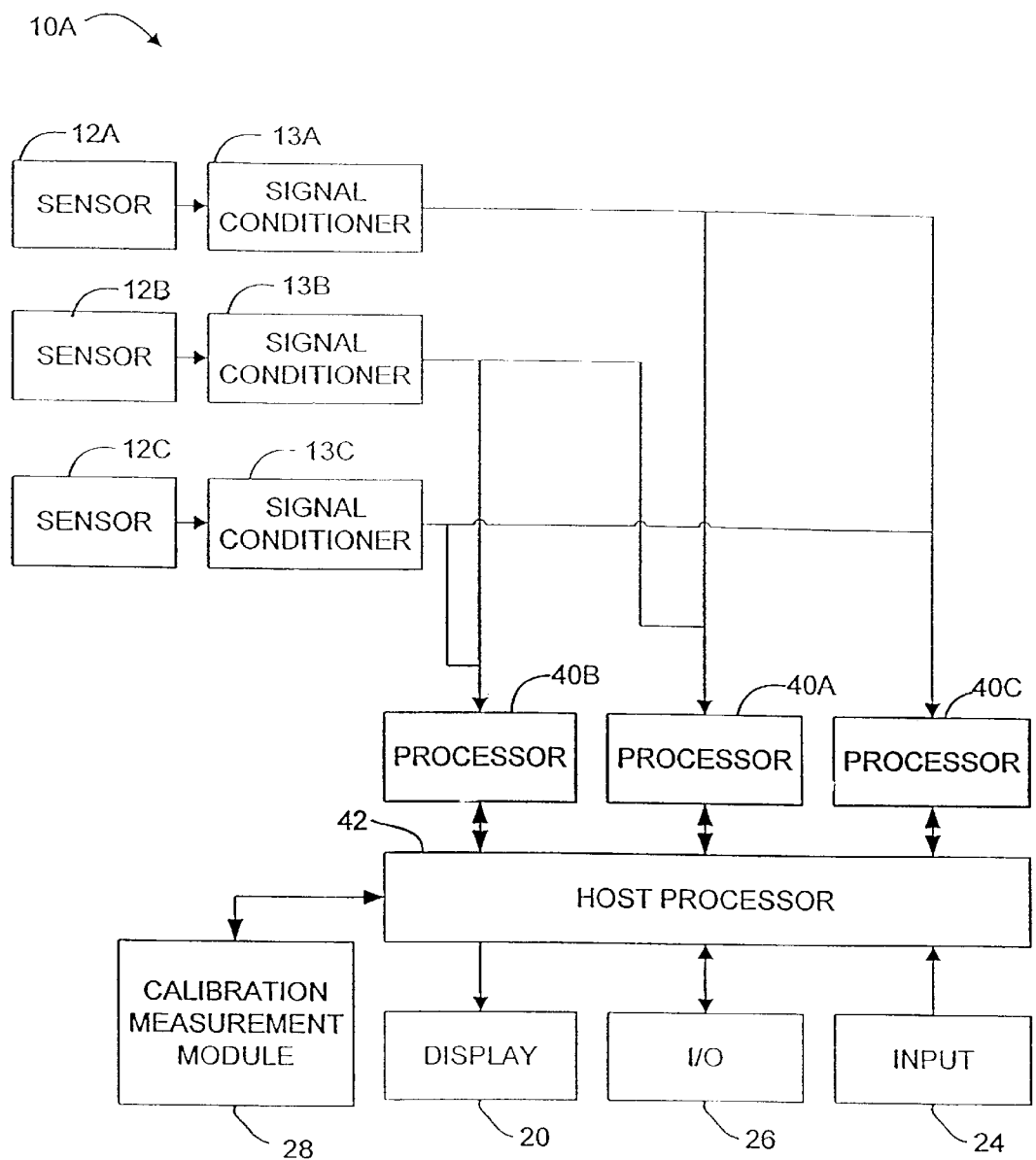

FIG. 3 illustrates apparatus 10A according to an alternative embodiment of the invention. Apparatus 10A comprises a separate processor 40 for computing the performance criterion and the blood pressure determined by each pair of sensors. For example, processor 40A computes the performance criterion and an estimated blood pressure from the signals measured by sensors 12A and 12B. Processor 40B computes the performance criterion and an estimated blood pressure from the signals produced by sensors 12B and 12C. Sensor 40C computes the performance criterion and an estimated blood pressure from the signals produced by sensors 12A and 12C. Each of processors 40 also computes values for oxygen saturation for one of the sensors. The results of the computations by the processors 40 are delivered to a host processor 42. Host processor 42 coordinates the operation of apparatus 10A and also computes an appropriate value for the systolic and diastolic blood pressures, pulse rate, blood volume and oxygen saturation from the received signals. In doing so, processor 42 may implement the functions of selection system 16 which is described above.

As will be apparent to those skilled in the art in the light of the foregoing disclosure, many alterations and modifications are possible in the practice of this invention without departing from the spirit or scope thereof. For example:

the number of sensors may be varied. If four sensors are used then there are potentially six pairs of sensors from which pulse transit time information for blood pressure estimation may be derived. There are four sensors from which pulse and oxygen saturation information may be derived.

various functions which are described above as being performed by software running on a computer processor may be performed using appropriate hardware.

Accordingly, the scope of the invention is to be construed in accordance with the substance defined by the following claims.

What is claimed is:

1. A method for monitoring vital signs of a subject, the method comprising:

a) placing a plurality of sensors at spaced apart locations on the body of a subject;

b) at a controller, receiving signals originating from the plurality of sensors;

c) taking the signals in each of a plurality of distinct group of the signals, each of the groups comprising enough of the sensors to determine a value for a vital sign, and for each group computing a performance criterion;

d) for each of one or more of the groups including at least a one of the groups corresponding to a best performance criterion, determining a group value for the vital sign; and, e) determining from the performance criterion and the group values an output value for the vital sign.

2. The method of claim 1 wherein the vital sign comprises a blood pressure, the groups each comprise signals from two sensors and determining a group value for the vital sign comprises measuring a differential pulse transit time from the signals from the two sensors.

3. The method of claim 2 wherein determining an output value for the vital sign comprises setting the output value equal to the group value for the one of the groups corresponding to the best performance criterion.

4. The method of claim 2 wherein determining an output value for the vital sign comprises computing a weighted average of the group values.

5. The method of claim 4 wherein computing the weighted average is performed substantially according to the formula:

$$P = \sum_{ij} a_{ij} P_{ij}$$

where $P_{ij}$ are the group values, i and j are indices which together identify one of the groups, $a_{ij}$ are weighting factors given by:

$$a_{ij} = \frac{C_{ij}}{\sum_{ij} C_{ij}}$$

and, $C_{ij}$ are the performance criteria.

6. The method of claim 1 comprising activating a warning signal if the performance criterion for any one of the groups falls below a threshold value.

7. The method of claim 1 comprising activating a warning signal if the performance criterion for any one of the groups falls below a threshold value and stays below the threshold value for a time longer than a threshold time.

8. The method of claim 2 wherein the performance criterion is a function of a difference between a value of a function of signals in a group and an average value for the function.

9. The method of claim 8 wherein computing the performance criterion comprising at least substantially computing a value for the function:

$$C_{ij} = [\text{Corr }(p_i, p_j) / \sigma_i \sigma_j]_{max}$$

where: $C_{ij}$ is a performance criterion for the group of sensors under consideration; Corr is a correlation function between the two signals ($p_i(t), p_j(t)$) and $\sigma_i$ and $\sigma_j$ are deviation measures of the two signals.

10. The method of claim 9 wherein Corr is determined by substantially performing the calculation:

$$\text{Corr}(p_i, p_j) = \frac{1}{N} \sum_{k=0}^{N-1} [p_i(k) - \mu_i][p_j(k) - \mu_j]$$

where N is a number of samples of pulse signals used to determine the performance of the considered pair of sensors in a certain period of time; and $\mu_i$ and $\mu_j$ are average values of the signals.

11. The method of claim 10 comprising obtaining values for $\sigma_i$ and $\sigma_j$ substantially by performing the computations:

$$\sigma_i = \sqrt{\frac{1}{N-1} \sum_{k=0}^{N-1} [p_i(k) - \mu_i]^2} \text{ and,}$$

$$\sigma_j = \sqrt{\frac{1}{N-1} \sum_{k=0}^{N-1} [p_j(k) - \mu_j]^2}.$$

12. The method of claim 10 comprising determining $\mu_i$ and $\mu_j$ substantially by computing the results:

$$\mu_i = \frac{1}{N} \sum_{k=0}^{N-1} p_i(k)$$

and, $$\mu_j = \frac{1}{N} \sum_{k=0}^{N-1} p_j(k).$$

13. The method of claim 1 wherein the vital sign is a blood oxygen saturation.

14. The method of claim 1 wherein the vital sign is a pulse rate.

15. The method of claim 1 wherein the vital sign is a blood volume.

16. Apparatus for monitoring vital signs of a subject, the apparatus comprising:
 a) a plurality of sensors;
 b) a controller connected to receive signals from the sensors, the controller comprising:
  i) means for taking the signals, in each of a plurality of distinct groups of the signals, each of the groups comprising enough of the sensors to determine a value for a vital sign, and for each group computing a performance criterion;
  ii) means for computing a value of the vital sign from the signals of each group;
  iii) means for computing a weighted average of values of the vital sign computed for the signals of each group;
  iv) means for displaying the weighted average.

17. The apparatus of claim 16 wherein the controller comprises a processor executing instructions of a software program.

18. The apparatus of claim 16 comprising means for taking a reliable reference value of the vital sign.

19. The apparatus of claim 18 wherein the vital sign is blood pressure and the means for computing a value of the vital sign from the signals of each group comprises means for determining a differential pulse transit time from the signals of each group and means for computing a blood pressure estimate from the differential pulse transit time and a known relationship between blood pressure and the differential pulse transit time.

20. Apparatus for monitoring a vital sign of a subject, the apparatus comprising:
 a) a processor;
 b) an interface conveying a plurality of digitized signals to the processor;
 c) a display connected to display data supplied by the processor; and,
 d) a program memory comprising a plurality of software instructions for execution on the processor, the plurality of software instructions comprising instructions which, when executed by the processor, cause the processor to:
  i) take a plurality of signals received at the interface in a plurality of distinct groups of the signals, each of the groups comprising enough of the signals to determine a value for a vital sign,
  ii) for each group compute a performance criterion;
  iii) for each of one or more of the groups including at least a one of the groups corresponding to a best computed performance criterion, determining a group value for the vital sign;
  iv) determine from the performance criterion and the group values an output value for the vital sign; and,
  v) display the output value for the vital sign on the display.

* * * * *